United States Patent [19]

Valeri

[11] Patent Number: 4,804,363

[45] Date of Patent: Feb. 14, 1989

[54] APPARATUS AND METHOD FOR STORING AND PROCESSING BLOOD

[75] Inventor: Cesare R. Valeri, Marblehead, Mass.

[73] Assignee: Autologous Blood Corporation, Miami, Fla.

[21] Appl. No.: 886,196

[22] Filed: Jul. 16, 1986

[51] Int. Cl.⁴ .......................................... A61M 37/00
[52] U.S. Cl. ...................... 604/6; 604/283; 604/408; 422/41; 210/198.1; 210/782
[58] Field of Search ..................... 604/408–415, 604/403, 516, 262, 283, 284, 905; 422/44, 41; 210/782, 198.1, 257.1

[56] References Cited

U.S. PATENT DOCUMENTS

| | | |
|---|---|---|
| 3,145,713 | 4/1964 | Latham . |
| 3,211,368 | 10/1965 | Shonley ............................. 604/410 |
| 3,328,255 | 6/1967 | Ilg . |
| 3,347,454 | 10/1967 | Bellamy . |
| 3,351,432 | 11/1967 | Van Dyke . |
| 3,452,924 | 7/1969 | Schultz ............................. 604/403 |
| 3,545,671 | 12/1970 | Ross . |
| 3,576,650 | 4/1971 | Underwood et al. ............. 604/408 |
| 3,625,212 | 12/1971 | Rosenberg . |
| 3,655,123 | 4/1972 | Judson . |
| 3,708,110 | 1/1973 | Unger . |
| 3,866,608 | 2/1975 | Reynolds . |
| 3,896,733 | 7/1975 | Rosenberg . |
| 3,905,477 | 9/1975 | Graham ............................. 604/408 |
| 3,942,529 | 3/1976 | Waage ............................... 604/408 |
| 3,954,414 | 5/1976 | Samson . |
| 3,965,896 | 6/1976 | Swank . |
| 4,004,586 | 1/1977 | Christensen et al. ............. 604/905 |
| 4,014,329 | 3/1977 | Welch . |

(List continued on next page.)

OTHER PUBLICATIONS

Table of Contents and Chapters 4 and 5 and Ch. 9 of book "Blood Banking and the Use of Frozen Blood Products", by C. R. Valeri, published in 1976.

(List continued on next page.)

Primary Examiner—C. Fred Rosenbaum
Assistant Examiner—Mario Costantino
Attorney, Agent, or Firm—Marshall, O'Toole, Gerstein, Murray & Bicknell

[57] ABSTRACT

This disclosure relates to a blood processing and preservation system. Apparatus of the system comprises a primary collection bag, a blood collection tube connected to the bag and adapted to draw a unit of blood from a person and feed the blood into the bag, and a harness connected to the bag for conducting solutions and blood components into and out of the bag. The harness includes a first tube for removing at least one blood component from the bag while retaining another component, a second tube for moving a cryoprotective solution into and out of the bag, a third tube for conducting a wash solution into and out of the bag, and identification on the bag. The foregoing apparatus is usable in a blood system including the method steps of collecting a unit of blood from a person and delivering the blood to the collection bag, processing the blood to separate the components and removing the components except for the red blood cells from the bag, preparing the red blood cells for freezing by conducting a cryoprotective solution into the bag and mixing this solution with the red blood cells, preserving the red blood cells by freezing, subsequently washing the red blood cells by conducting a wash solution and the cells into and out of the bag, and delivering the cells in the same collection bag to a recipient. While the foregoing method may be used in a homologous blood system where the recipient is not the donor, it is especially suited for use in an autologous blood system where the blood is reinfused in the person who furnished the blood, and the identification on the bag assures the recipient that he/she is receiving his/her own blood. Other blood components, such as the plasma, may also be preserved by freezing.

14 Claims, 4 Drawing Sheets

U.S. PATENT DOCUMENTS

| | | |
|---|---|---|
| 4,033,345 | 7/1977 | Sorenson . |
| 4,047,526 | 9/1977 | Reynolds . |
| 4,150,673 | 4/1979 | Watt . |
| 4,160,473 | 7/1979 | Winchell .......................... 604/409 |
| 4,222,379 | 9/1980 | Smith ................................ 604/410 |
| 4,223,675 | 9/1980 | Williams ........................... 604/410 |
| 4,474,568 | 10/1984 | Schoendorfer . |
| 4,501,581 | 2/1985 | Kurtz . |
| 4,547,186 | 10/1985 | Bartlett . |
| 4,564,359 | 1/1986 | Ruhland . |
| 4,565,073 | 1/1986 | Lavender . |
| 4,573,974 | 3/1986 | Ruschke . |
| 4,573,980 | 3/1986 | Karrasch . |
| 4,573,992 | 3/1986 | Marx . |
| 4,609,372 | 9/1986 | Carmen . |

OTHER PUBLICATIONS

Publication "Transfusion", by Valeri et al., Mar.-Apr. 1981, vol. 21, No. 2.

Journal published by CRC Press, Inc., titled "Critical Reviews in Clinical Laboratory sciences", vol. 17, Issue 4, dated 1982, pp. 326 through 359, by Valeri.

Paper titled "Status Report on Rejuvenation and Freezing of Red Blood Cells", by Captain C. R. Valeri, published in 1981.

APPARATUS AND METHOD FOR STORING AND PROCESSING BLOOD

FIELD AND BACKGROUND OF THE INVENTION

This invention relates to a method and apparatus for collecting, freezing and preserving, and preparing for reinfusion of blood components.

It has been common practice for many years to collect blood from donors, process the blood components and preserve some of the components for a short time, and then deliver the preserved component to a patient who is in need of the blood. Plastic collection bags, tube harnesses, and transfusion sets are commercially available for this purpose.

Procedures are also known for freezing blood components, and blood processing machines are commercially available for preparing a blood component after freezing and prior to infusion into a patient. The Samson et al. U.S. Pat. No. 3,954,414, for example, describes a machine for processing frozen blood cells, and the Lavender U.S. Pat. No. 4,565,073 describes apparatus for use in freezing a blood component. It has been known for quite some time that blood components may be frozen at $-80°$ C. for 2-3 years and then safely reinfused, and recently it has been learned that blood components may be stored at this temperature for 20 years or more.

Further, systems have been described for removing blood from a person and then reinfusing the blood in the same person. For example, the Reynolds et al. U.S. Pat. No. 4,047,526 describes an "autologous blood system," and the Bartlett U.S. Pat. No. 4,547,186 describes an "autotransfusion system," wherein shed blood is recovered during an operation and reinfused in the patient. The Rosenberg U.S. Pat. No. 3,625,212 describes a plasmapheresis system wherein blood is extracted and processed, and the red blood cells are returned to the same individual; a safety arrangement is provided to ensure that the cells are not given to a different person.

The methods and apparatus of the prior art are not, however, suited for the processing and storage of blood components through numerous steps which may extend over a long period of time, while also providing certainty as to the identification of the person from which the blood was collected.

It is a general object of the present invention to provide improved apparatus and method for avoiding the problems of the prior art.

BRIEF SUMMARY OF THE INVENTION

Apparatus in accordance with this invention comprises a primary collection bag, blood collection means connected to the bag and adapted to draw a unit of blood from a person and feed the blood into the bag, and a harness connected to the bag for conducting solutions and blood components into and out of the bag. The harness means includes first tube means for removing at least one blood component from the bag while retaining another component, second tube means for moving a cryoprotective solution into and out of the bag, third tube means for conducting a wash solution into and out of the bag and reinfusing the blood component back into the collection bag, and identification means on the bag.

The foregoing apparatus is usable in a blood system including the method steps of collecting a unit of blood from a person and delivering the blood to the collection bag, processing the blood to separate the components and removing the components except for one remaining component from the bag, preparing the remaining component for freezing by conducting a cryoprotective solution into the bag and mixing this solution with the remaining component, preserving by freezing the remaining component, subsequently preparing the remaining component by conducting a wash solution and the cells into and out of the bag, and delivering the component in the same collection bag to a recipient.

While the foregoing method may be used in a homologous blood system where the recipient is not the person who furnished the blood, it is preferably used in an autologous blood system where the blood is reinfused in the furnisher, and the identification means on the bag assures the recipient that he/she is receiving his/her own blood. Various blood components, such as the red blood cells and the plasma, may be preserved by freezing.

BRIEF DESCRIPTION OF THE DRAWINGS

The invention will be better understood from the following detailed description taken in conjunction with the accompanying figures of the drawings, wherein.

DETAILED DESCRIPTION OF THE DRAWINGS

Figure 1:
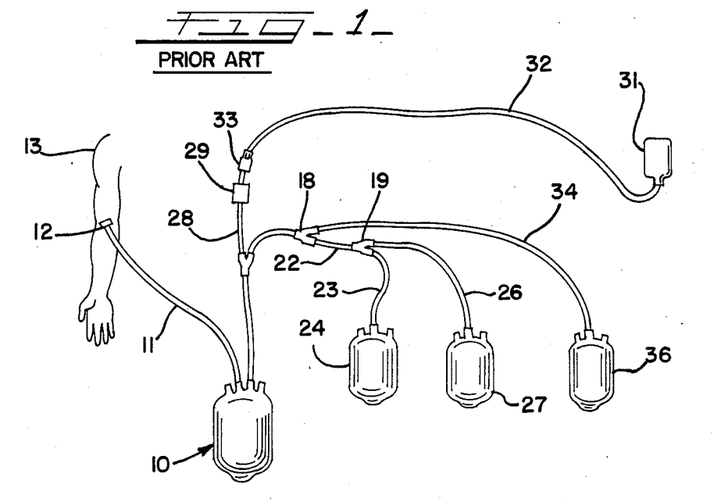
FIG. 1 is a diagram of apparatus in accordance with the prior art.

FIG. 1 illustrates a prior art bag and tube harness for collecting and processing blood. This structure is known in the prior art and has been provided by Fenwal Laboratories Division of Travenol Laboratories, Inc. Connected to a primary collection bag 10 is a flexible tube 11 and a needle 12 for insertion into the arm 13 of a person furnishing blood, in order to draw blood from the person and feed the blood through the tube 11 into the collection bag 10. The bag is made, for example, of polyvinylchloride (PVC) and has an 800 ml capacity, and normally approximately 450 ml of blood is collected in the bag 10. The bag 10 is received from the manufacturer with an anti-coagulant in it which is mixed with the blood as it is drawn from the person 13. For example, 63 ml of citrate-phosphate-dextrose (CPD) is in the bag and mixed with the collected blood. After the blood has been collected, the needle 12 is withdrawn from the person and the tube 11 may be heat sealed and then severed.

The apparatus shown in FIG. 1 also includes provision for separating the blood into its components and preserving at least some of the components. To this end, a second tube 16 is attached to the bag 10 and the tube 16 is connected, through wye connectors 17, 18 and 19, and through tube sections 21, 22, 23, 26 and 34, to secondary bags 24, 27 and 36. After the blood has been collected in the primary collection bag 10, it is placed in a centrifuge which separates the red blood cells from the plasma and the other blood components, and the plasma and the other components are then drawn off through the tubes and into the bags 24 and 27. The bags 24 and 27 may then be removed by heat sealing and severing the attached tubes.

It has also been known in the prior art that red blood cells may be preserved by freezing. To this end, the tube harness further includes another tube 28 which is connected between a sealed port 29 and the wye connector 17. Prior to preserving the red blood cells by freezing, a bottle 31 containing a glycerol solution is connected by a tube 32 and a port 33 to the port 29, and the glycerol solution is fed through the tubes 16, 28 and 32 into the primary collection bag 10 and mixed with the red blood cells. After mixing, the supernatant glycerol is drawn from the primary collection bag 10 through the tubes 16, 21 and 34, and fed to the secondary bag 36.

In the prior art, the glycerolized red blood cells are then frozen in the primary bag 10. When the blood cells are to be infused in a recipient, the bag 10 and the red blood cells are thawed, and the red blood cells are then drained from the bag 10 into a conventional blood processor and the bag 10 is discarded. The glycerol is washed from the red blood cells, and the red blood cells are then removed from the blood processor and fed into a clean bag which is used to deliver the cells to a recipient.

The structure shown in FIG. 1 and the method steps outlined above have been used in homologous blood systems wherein units of blood are received from donors, blood components stored, then processed and infused into recipients as needed. A problem with the structure and method described in connection with FIG. 1 is that the blood in a homologous system may carry diseases such as hepatitis and AIDS which infect the recipient.

An autologous blood system in accordance with a preferred form of the present invention avoids the foregoing problem by collecting blood from a person in a collection bag, identifying the bag with the person, processing and preserving a blood component in the same bag, processing the blood component in the bag and a processing machine, and returning in the same bag in the blood component to the individual who initially furnished the blood, so that the recipient has confidence that the blood component he/she is receiving is in fact the blood he/she previously furnished.

Figure 2:
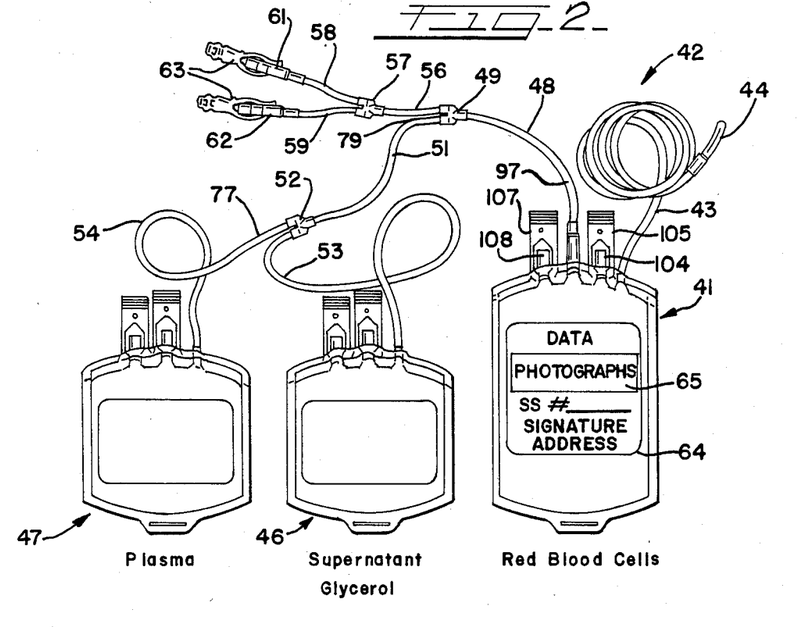
FIG. 2 is a diagram of apparatus in accordance with this invention.

With reference to FIG. 2, apparatus in accordance with the present invention comprises a primary collection bag 41 and a tube and secondary bag harness 42. These parts may be made of polyvinylchloride. The primary bag 41 may be essentially the same as the bag 10 shown in FIG. 1, and preferably comprises an 800 ml bag containing an amount of an anti-coagulant as previously described. Attached to the bag 41 is a tube 43 and a needle at the outer end of the tube, similar to the prior art arrangement. A sterile cover 44 normally covers the needle prior to use.

The tube and bag harness includes a secondary bag 46 designed to receive supernatant glycerol as will be described hereinafter, and a secondary bag 47 which receives plasma as will also be described hereinafter. The two secondary bags 46 and 47 are connected to the primary collection bag 41 by the tube harness 42 including a tube 48 connected between the primary bag 41 and a wye connector 49, another tube 51 connected between one branch of the wye connector 49 and another wye connector 52, and two tubes 53 and 54 connected between the two branches of the connector 52 and the two secondary bags 46 and 47, respectively. The wye connector 49 also has two branches, one of the branches being connected to the tube 51 and the second branch being connected to another tube 56 which extends to the center or common leg of another wye connector 57. The two branches of the wye connector 57 are connected to two tubes 58 and 59 which have ports 61 and 62 connected to their terminal ends. Sterile covers 63 are fastened over the ports 61 and 62 prior to use, and the two tubes 58 and 59 are preferably at least four inches long. The entire bag and tube harness assembly shown in FIG. 2 forms a sterile closed system.

Figure 5:
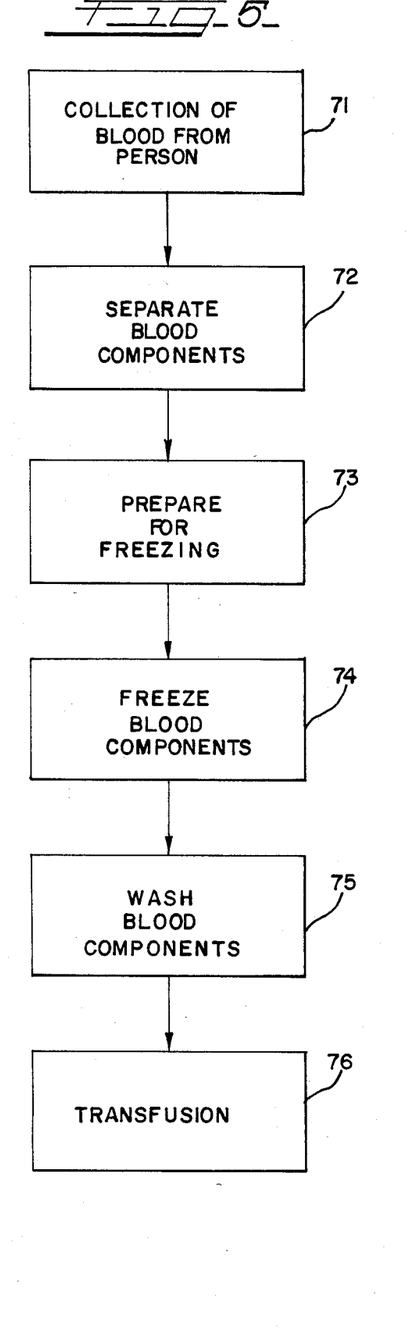
FIG. 5 is a diagram showing method steps in a system of this invention.

FIG. 5 illustrates the steps in a preferred form of the invention, utilizing the assembly shown in FIG. 2. At step 71, blood is drawn from a person by hanging the primary collection bag 41 with the assembly 42 attached to it, removing the cover 44 from the needle and inserting the needle into the arm of the person. A unit, such as 450 ml, of blood is collected in the primary collection bag 41, and as previously mentioned the blood is mixed in the bag 41 with the anti-coagulant already contained in the bag 41. The anti-coagulant in the bag 41 is preferably approximately 63 ml of CPD or CPD-A1. After collection of the blood, the needle is removed and the tube 43 is heat sealed, severed and discarded.

At the time of collection of the blood, an identification of the donor is connected to the bag 41. This identification may take the form of a label 64 which is permanently affixed to the outside of the bag. The label contains identifiers such as photographs 65 of the person, the signature, address and social security number of the person, and the date of collection. The person may also place any other personal identifier on the label, as desired.

At step 72, the red blood cells are separated in the primary collection bag 41 from the plasma and other components. This is accomplished by, within six hours of the collection of the blood, placing the bag in a conventional refrigerated blood centrifuge, and centrifuging the blood in a conventional manner. For example, the bag is centrifuged at 3700 rpm for approximately 10 minutes to prepare a red blood cell concentrate having a hematocrit value of approximately 80 V%. Thereafter, all of the plasma is removed to the secondary plasma bag 47 through the tubes 48, 51 and 54, and the tube 54 is then heat sealed and severed at approximately the point indicated by the numeral 77. It is preferred that the bag 41 containing the red blood cell concentrate and the remainder of the tube harness 42 be stored at approximately 4° C. for about three to five days before being frozen. The plasma in the secondary bag 47 also contains a quantity of the anti-coagulant which was mixed with the blood in the primary bag 41. It is preferred that a quantity of the plasma be removed from the secondary bag 47 and placed in two 2 ml provials (shown in FIG. 3 and indicated by the numeral 83). These two provials may be frozen along with the red blood cells in the bag 41 and are available for testing at a later date to determine whether the blood contains diseases. As will be described hereinafter, the remainder of the plasma in the secondary bag 47 may also be frozen and made available for use at a later date.

At step 73, the red blood cells in the bag 41 are prepared for freezing by adding the cryoprotective glycerol solution. This is accomplished by inserting the glycerol solution in the primary collection bag 41 through the port 61 (after removing the cover 63) and the tubes 58, 56 and 48. First the red blood cell concentrate is stored after collection at approximately 4° C. for approximately 3-5 days as previously mentioned. At the time of glycerolization, the glycerol solution and the red blood cells are brought to room temperature (between 22° and 30° C.), and the bag 41 containing the red blood cells is placed on a shaker platform. A container (not shown) of the glycerol solution is attached to the port 61 by means of, for example, the ports provided by the previously mentioned Fenwal Laboratories or a sterile docking apparatus such as that supplied by the E. I. du Pont Company. As a specific example, assume that the primary bag 41 contains between 231 and 280 grams of red blood cell concentrate having a hematocrit of approximately 80% V. The glycerol solution is added to the bag 41 in three steps. First, approximately 50 ml of the glycerol solution is fed into the primary bag 41 while the shaker platform is turned on. The shaker platform is then turned off and the solution in the primary bag 41 is allowed to equalibrate for approximately five minutes. The shaker platform is then turned on again (in both instances, the shaker platform is operated at a relatively low speed of approximately 180 oscillations per minute), and a second volume of approximately 50 ml of glycerol solution is added to the primary bag. The shaker platform is then turned off and the mixture is allowed to equalibrate for approximately two minutes. The primary bag 41 is then removed from the shaker platform, and, while applying continuous vigorous manual agitation to the mixture in the primary bag, a third volume of approximately 400 ml of glycerol solution is fed into the primary bag. The tube 58 is then heat sealed and severed at approximately the position indicated by the reference numeral 78. The empty glycerol container may then be discarded.

Thereafter, the primary bag 41 containing the red blood cells and the glycerol solution is placed in a centrifuge to concentrate the glycerolized red blood cells. The bag 41 is then removed from the centrifuge and placed in a plasma extractor, and the supernatant glycerol solution in the primary bag 41 is then removed from the primary bag and fed into the secondary bag 46 through the tubes 48, 51, and 53. Thereafter, the tube 51 is heat sealed and severed at approximately the location indicated by the reference numeral 79. At this point, the assembly shown in FIG. 2 is reduced to the primary collection bag 41, the tube 48, the wye connector 49, the tube 56, the wye connector 57, the tube 59, the port 62 and cover 63 (see FIG. 3).

Figure 3:
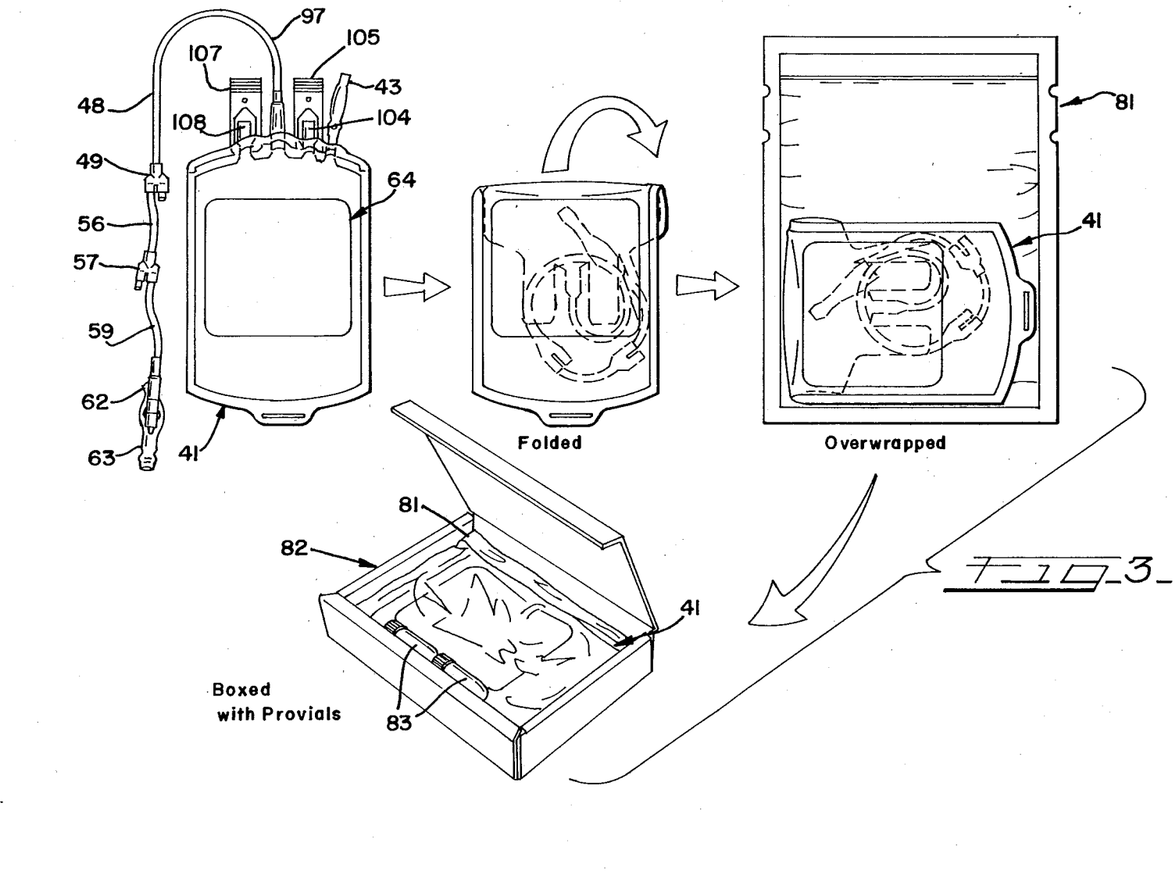
FIG. 3 is a diagram showing the preparation of a collection bag for freezing.

The primary bag 41 containing the glycerolized red blood cells is then further prepared for storage by, with reference to FIG. 3, placing the bag 41 in a plastic bag overwrap 81. Prior to placing the bag 41 in the bag overwrap 81, the upper end of the collection bag 41 and the remainder of the tube harness is preferably folded against the side of the primary bag. As much air as possible is squeezed out of the overwrap bag 81 and the bag 81 is then heat sealed. The bag 81 containing the collection bag 41 is placed in a storage box or container 82 along with the previously mentioned two provials 83 of plasma. Preferably the carton 82 is given identifying information generally comparable to that on the label 64 attached to the bag 41. The carton, after being closed and taped, is placed in a freezer and frozen at approximately −80° C.

It should be noted that the glycerolization process described above should be completed as quickly as possible. No more than four hours should be allowed to lapse between the time the bag 41 containing the red blood cells is removed from the 4° C. refrigerator and the time the bag is placed in the −80° C. freezer. The final concentration of glycerol in the bag 41 at the time of freezing is approximately 40% W/V and the hematocrit of the glycerolized solution is approximately 60±5% V.

At step 75 (FIG. 5) the red blood cells in the primary bag 41 are prepared just prior to the time of infusion, by removing the carton 82 from the freezer and removing the bag 41, and then thawing the red blood cells. The red blood cells are thawed in the bag 41 and in the overwrap bag 81 relatively rapidly by, for example, immersing the bag 81 in a heated water bath which is maintained at approximately 42° C., for approximately 20-25 minutes. The red blood cells in the bag 41 are warmed to a temperature of approximately 20° C. The purpose of the overwrap bag 81 is to prevent the possibility of contamination of the collection bag 41 by the warming water. During the warming or thawing process, care must be taken not to leave the bag in the 42° C. warming water for more than about 40 minutes because prolonged exposure of the red blood cells to the warming water may harm the red blood cells. After thawing, the overwrap bag 81 is removed from the collection bag 41, and the red blood cells are then washed in a blood processing machine to remove the glycerol solution.

Figure 4:
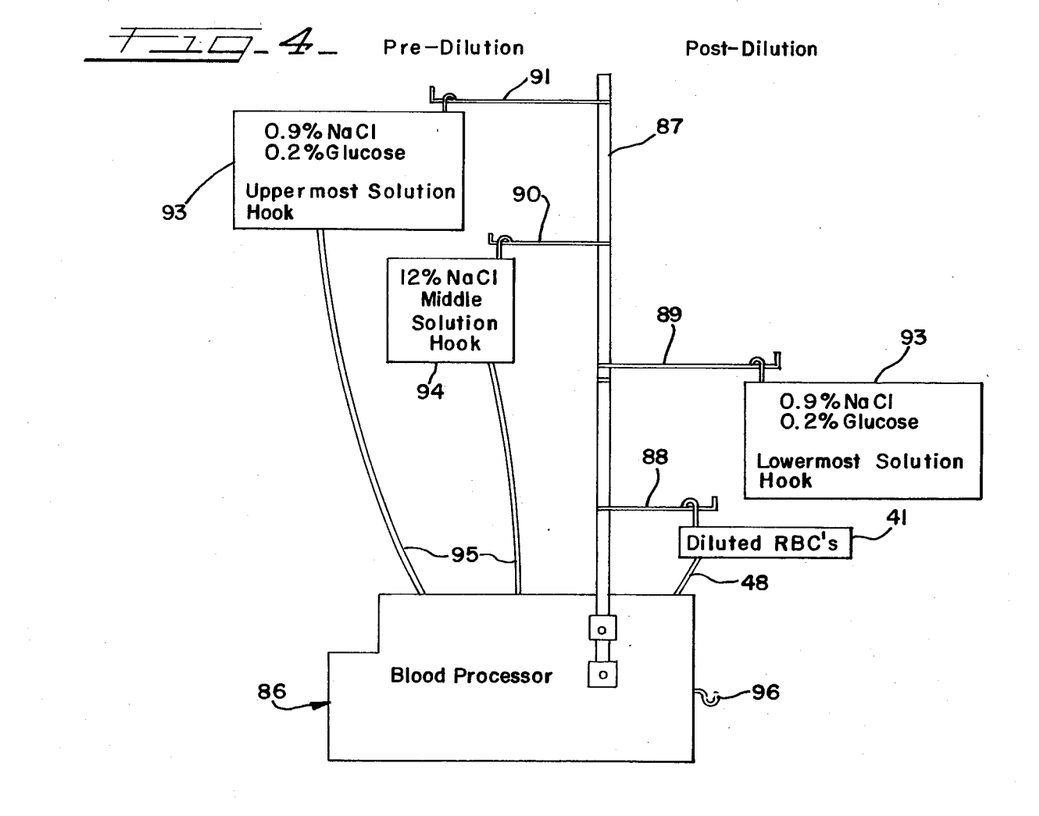
FIG. 4 is a diagram showing apparatus for washing a blood component after freezing.

With specific reference to FIG. 4, the cells are washed using, for example, a conventional Haemonetics Blood Processor No. 115. The blood processor is indicated by the reference numeral 86 and includes a shaker platform, a centrifuge and a wash bowl. Since these articles are well known to those skilled in the art, they are not illustrated and described in detail. Further included are support pole 87 and a plurality of support arms or hooks 88 through 91 which are attached to the support pole 87. Also provided are a first container 93 of a 0.9% sodium chloride and 0.2% glucose solution, and a second container 94 containing a 12% sodium chloride solution. The machine 86 is a gravity feed machine, and the container 93 is initially hung on the support arm 91 which is at an elevation of approximately 34" above the machine 86. The other container 94 is hung on the support arm 90 which is at an elevation of approximately 24". The support arm 88 for the bag 41 containing the red blood cells is mounted at approximately 6", and the support arm 89 is located at approximately 12". In the specific example being described herein, the container 94 holds at least 50 ml of a wash solution in which each 100 ml contains 12 grams sodium chloride USP. The container 93 holds at least 1.5 liters, and each 100 ml contains 200 mg of glucose (hydrous) USP and 900 mg sodium chloride USP.

A closed clamp is located on the tube 48 of the bag 41, and closed clamps are placed on tubes 95 leading from the two containers 93 and 94 to the machine. The tubes 95 leading from the two containers 93 and 94 are aseptically connected between the containers and the blood processor such that the solutions flow by gravity from the containers when the clamps are opened. Further, the machine 86 is aseptically connected to the port 62 of the harness 42. This may be accomplished using a Fenwal Laboratories port or a sterile docking device as previously mentioned.

The bag 41 is first placed on a shaker platform of the machine 86. For the initial dilution, the shaker of the machine 86 is turned on and the clamps on the tube 48 connecting the bag 41 with the machine 86 and the tube 95 connecting the container 94 with the machine 86 are opened. 50 ml of the solution from the container 94 are drained into the bag 41 and mixed with the cells by the agitation of the shaker, and the clamp on the tube from the container 94 is closed. The shaker is then turned off and the solution is allowed to equilibrate for at least two minutes. The shaker is again turned on and the clamp on the tubing leaving the container 93 is opened, and approximately 100 ml of the solution from the container 93 is allowed to enter the bag 41 and mix with the solution already in the bag. After approximately 100 ml of this solution has entered the bag 41, the tube is again closed by the clamp, and the shaker is turned off. The red blood cells and the wash solution are then allowed to equilibrate for at least two minutes. After this two minute period, the shaker is again turned on and the tubing leaving the container 93 is again opened and approximately 150 ml of the solution is drained to the bag 41 and mixed with the previous solution. The clamp on the tube leaving the container 93 is again closed and the shaker turned off, and the solution in the bag is allowed to equilibrate for another two minutes.

After the two wash solutions have been placed in the bag 41 and mixed with the red blood cells, the clamp to the bag 41 is closed and the bag 41 is inverted and hung from the support arm 88. Further, the container 93, with its associated tube clamp closed, is relocated from the support arm 91 to the lower support arm 89. The centrifuge of the machine 86 is then turned on, and the clamp on the tubing leading from the bag 41 is opened. After some of the red blood cells and wash solution mixture have drained from the bag 41 and into the wash bowl of the centrifuge and the supernatant appears in the plastic bag to collect the waste solution, the clamp on the tubing leading from the container 93 is also opened, and additional wash solution from the container 93 is allowed to flow into the wash bowl along with the diluted red blood cells. When all of the diluted red blood cells have been drained from the bag 41 and into the wash bowl of the centrifuge, the essentially empty bag 41 is removed from the support arm 88 and lowered. The tube of the machine 86 leading to the wash bowl is momentarily closed, as by pinching it, causing wash solution draining from the container 93 to flow into the bag 41. After approximately 20-30 ml of the wash solution has moved from the container 93 into the bag 41, the bag 41 is returned to the support arm 88 and the tubings are opened, allowing any residual red blood cells and the wash solution to drain from the bag 41 and into the wash bowl. This rinsing procedure is preferably repeated at least once more to make certain that all residual red blood cells are removed from the bag 41 and from the connecting tubing. The clamp on the tubing between the bag 41 and the machine 86 is then closed. After a total of approximately 1500 ml of the wash solution has drained from the container 93, the clamp on the tubing leaving the container 93 is closed and the centrifuge is turned off. At this point the centrifuge has operated for up to fifteen minutes and the washed red blood cells are separated from the remainder of the solution. When the wash bowl has stopped rotating, the primary bag 41 is removed from the support arm 88 and hung from a lower support hook 96 on the side of the machine, and the clamp on the tubing between the wash bowl and the bag 41 is then opened. The red blood cells in the wash bowl (separated from the glycerol and the wash solution) are then caused to flow from the wash bowl and to return through the port 62 and the tube 48 to the primary collection bag 41. After the bowl has been emptied of the red blood cells, the tubing 48 is heat sealed and severed at approximately the location indicated by the reference numeral 97 in FIGS. 2 and 3, and the bag 41 is removed from the machine.

As previously mentioned, the foregoing wash sequence should be completed within two hours of the thawing of the red blood cells so that the washed blood cells may be returned to a refrigerator. After removal from the wash machine, the red blood cells in the bag 41 may be stored at approximately 4° C. for not more than 72 hours, if the red blood cells are not used immediately.

Figure 6:
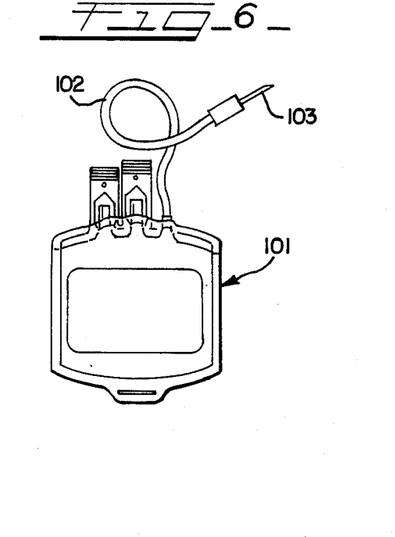
FIGS. 6 and 7 show apparatus for use with the bag just prior to and at the time of infusion.
Figure 7:
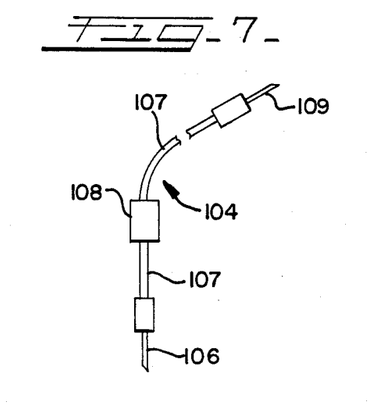

As previously mentioned, in an autologous blood system in accordance with the preferred embodiment of the invention, the red blood cells in the bag 41 are returned to the same person from whom they were initially drawn. When needed by the person, the bag 41 containing the cells is retrieved from the freezer and prepared by washing as described above and then delivered to the person. Just before transfusion, the washed red cells in the bag 41 are preferably concentrated by centrifugation at approximately 3400 rpm for 4 minutes, for example, and any supernatant solution is removed. To remove this supernatant solution, a transfer bag 101 (FIG. 6) is sterilely connected to the collection bag 41 by a tube 102 and a stylet 103. With reference to FIGS. 2 and 3, it will be noted that the collection bag 41 contains a port 104 which is sealed by a cover 105. The stylet 103 is pressed through the cover 105 and the port 104, thereby enabling the supernatant solution to be removed from the bag 41. To infuse the concentrated red blood cells into the patient, a transfusion set 104 shown in FIG. 7 is connected to the bag 41. The transfusion set 104 includes a stylet 106 which is connected to the primary collection bag 41 by inserting it through another cover 107 and into a port 108 of the bag 41. The stylet 106 is connected by a tube 107 to a filter 108 and a needle 109 which is inserted into the person. The infusion process is, of course, conducted in the customary manner.

From the foregoing it will be apparent that novel and improved autologous blood system has been provided. A sterile closed assembly is provided, including an identification of the person from whom the blood was received. A single primary blood collection bag is used from the time of initial collection, through the separation of the blood components, glycerolization, freezing, preparation and washing, to the infusion of the blood. The identification on the label provides the person with assurance that the blood component in the bag was drawn from him/her. The provials are available for tests prior to infusion to determine the presence of any disease in the blood.

The blood components could instead be infused into a person other than the original donor. The assembly and method described herein may also be used in homologous blood systems wherein it is desired to use a closed sterile assembly including primary and secondary bags and two ports.

While the description herein has been concerned with the processing and preservation of red blood cells, it should be understood that other blood components could be preserved in addition to or in place of the red blood cells. Blood plasma, for example, may be sealed and preserved in the secondary bag 47 after separation from the red blood cells. The plasma so obtained may be preserved in a fresh liquid condition for a relatively short time, or it may be preserved by freezing at, for example, $-80°$ C. for long term storage. Plasma may be frozen without a cryoprotective solution, and therefore it is not necessary to mix the plasma with glycerol before freezing and later to wash the plasma after thawing.

I claim:

1. A method of processing blood utilizing a sterile closed assembly including a primary bag having an anticoagulant therein, and a sterilely closed tube harness including a first tube connected to the primary bag, a secondary tube connected to the first tube and first and second sealed ports connected to the first tube, comprising the steps of:
   (a) collecting blood from a donor in said primary bag and mixing in said primary bag said blood and said anticoagulant;
   (b) separating said blood in said primary bag into a plurality of blood components;
   (c) retaining in said primary bag a unit of one of said components while removing through said first tube to said secondary tube the remainder of said components;
   (cc) sealing off and removing said secondary tube from said first tube;
   (d) sterilely connected to said first port a supply of cryoprotective solution;
   (e) feeding said solution into said primary bag through said first port and said first tube and mixing said solution with said unit in said primary bag;
   (ee) sealing off and removing said first port from said first tube;
   (f) freezing the mixture of said unit and said solution in said primary bag;
   (g) subsequently thawing said mixture in said primary bag;
   (h) sterilely connecting said second port to a blood processor and a supply of wash solution;
   (i) flowing said mixture through said second port to said processor and combining said wash solution with said mixture in said processor;
   (j) separating said wash solution and said cryoprotective solution from said unit, flowing said unit into said primary bag through said first tube and said second port; and
   (k) removing said primary bag from said blood processor.

2. A method according to claim 1, and further including the step of preparing an identification of said donor, and connecting said identification to said primary bag.

3. A method according to claim 2, and further including the step of administering said blood component to said donor.

4. A method according to claim 1, wherein said unit of one of said components comprises a unit of red blood cells.

5. A method according to claim 1, wherein said tube harness further includes at least one secondary bag connected to said secondary tube, and wherein said remainder of said blood components removed to said secondary tube are flowed into said one secondary bag.

6. A method according to claim 5, wherein blood plasma is flowed into said secondary bag.

7. A method according to claim 1, wherein said tube harness further includes at least one secondary bag connected to said first tube, and further comprising the step after step (e) of flowing any supernatant cryoprotective solution into said secondary bag.

8. A method according to claim 1, and further including the step after step (h) of flowing a portion of said wash solution into said primary bag and mixing with said mixture.

9. A method according to claim 8, wherein said one of said components comprises red blood cells, and further comprising the step of preparing an identification of said donor, and connecting said identification to said primary bag.

10. A method according to claim 9, wherein said step of freezing said mixture in said primary bag comprises bringing the temperature thereof to approximately $-80°$ C.

11. A method according to claim 1, and further including the step after step (j) of sealing off and removing said first tube from said primary bag.

12. A method according to claim 1, and further including the step after step (k) of refrigerating said primary bag and said unit of blood.

13. A method according to claim 1, and further including the step after step (ee) of wrapping said primary bag in a sealed container, and subsequently thawing the primary bag and the mixture while wrapped in said sealed container.

14. A method of processing a blood component which has been frozen in a collection bag, the bag containing a mixture of the blood component and a cryoprotective agent, and the collection bag having a sterile tube connected thereto, said method comprising the steps of thawing said blood component in said bag, flowing a quantity of wash solution into said bag and forming in said bag a mixture of cryoprotective agent, wash solution and blood component, flowing said mixture into a separator and separating said blood component from the cryoprotective agent and the wash solution, and returning the blood component to the collection bag.

* * * * *

UNITED STATES PATENT AND TRADEMARK OFFICE
CERTIFICATE OF CORRECTION

PATENT NO. : 4,804,363
DATED : February 14, 1989
INVENTOR(S) : Cesare R. VALERI

It is certified that error appears in the above-identified patent and that said Letters Patent is hereby corrected as shown below:

Column 1, between lines 3 and 5,
insert the following statement;

--This invention was made with Government support under Contract N00014-79-C-0168 awarded by the Department of the Navy. The Government has certain rights in the invention.--

Signed and Sealed this

Twenty-fifth Day of February, 1992

Attest:

HARRY F. MANBECK, JR.

Attesting Officer

Commissioner of Patents and Trademarks